United States Patent [19]

Hiraki et al.

[11] Patent Number: 5,759,844
[45] Date of Patent: Jun. 2, 1998

[54] ANTIBACTERIAL ARTICLES AND METHODS OF PRODUCING THE ARTICLES

[75] Inventors: Jun Hiraki; Sumiko Watanabe; Masamichi Muto, all of Yokohama, Japan

[73] Assignee: Chisso Corporation, Osaka, Japan

[21] Appl. No.: 568,381

[22] Filed: Dec. 6, 1995

[30] Foreign Application Priority Data

Dec. 22, 1994 [JP] Japan .................................. 6-336387

[51] Int. Cl.⁶ .......................................... C12N 1/06
[52] U.S. Cl. .......................... 435/259; 427/430.1
[58] Field of Search ........................... 435/317.1, 325, 435/259; 427/430.1

[56] References Cited

PUBLICATIONS

Shima et al. The Journal of Antibiotics. vol. XXXVII. pp. 1449–1455. Nov. 1984.

*Primary Examiner*—Leon B. Lankford, Jr.
*Attorney, Agent, or Firm*—Leydig, Voit & Mayer, Ltd.

[57] ABSTRACT

An antibacterial article inhibits the proliferation of microorganisms on the surface of food. The antibacterial article includes a substrate, such as a nonwoven material, on which is adsorbed ε-polylysine. The article is produced by applying an aqueous or alcoholic solution of ε-polylysine to the substrate by spraying or immersion.

9 Claims, No Drawings

ANTIBACTERIAL ARTICLES AND METHODS OF PRODUCING THE ARTICLES

FIELD OF THE INVENTION

The present invention relates to antibacterial materials including ε-polylysine adsorbed on fibers, nonwoven fabrics, knitted or woven fabrics, films, sheets and the like to inhibit proliferation of micro-organisms in the vicinity of the materials or in food preventing decomposition of food and inhibiting proliferation of micro-organisms.

DESCRIPTION OF THE PRIOR ART

Hitherto, for preventing decomposition of food, there are known methods for directly adding various kinds of food preservatives or materials having an antibacterial effect such as alcohol. A water absorbent sheet is used to prevent the deterioration of the outward appearance of food based on surplus water content. However, the sheet does not in preventing proliferation of micro-organisms adhered to food.

Conventionally when food preservatives or materials having antibacterial effect are directly added to food, it is necessary to uniformly add them to inhibit the proliferation of micro-organisms adhered to food packages or micro-organisms in the surroundings. Such additives have an adverse effect upon the physical properties and taste of food. When the food preservatives are directly sprayed on food, since they are scattered in the atmosphere and a little of them are adhered to food, it is necessary to spray them to an excess. Then, the taste of food suffers and the working atmosphere is adversely affected.

The antibacterial effect of ε-polylysine is well-known. ε-polylysine has been used for preventing proliferation of micro-organisms in food by kneading it together with food or directly spraying it on food. However, in the case of direct addition of the ε-polylysine to food, the added amount is influenced by the kinds or forms of food, and is about 100 mg per 1 kg of food. If the amount is in excess, it adversely affects food taste and physical properties.

A water absorbent sheet is, further, used for preventing deterioration in the outward appearance of food based on excess water content, so that the sheet does not inhibit proliferation of micro-organisms.

The present invention aims to inhibit proliferation of micro-organisms at the contact surface of food, to prevent deterioration of the taste of food, and to provide antibacterial materials having high safety without adversely influencing the surroundings.

SUMMARY OF THE INVENTION

The present invention resides in the following items of (1), (2) and (3).

(1) An antibacterial article including adsorbed ε-polylysine.

(2) A process for producing an antibacterial article, characterized in that the article is obtained by immersing a substrate for the antibacterial article in an aqueous solution of ε-polylysine or a solution of ε-polylysine in an alcohol or in an aqueous solution containing an alcohol.

(3) A process for producing an antibacterial article, characterized in that the article is obtained by spraying an aqueous solution of ε-polylysine or a solution of ε-polylysine in an alcohol or in an aqueous solution containing an alcohol on a substrate for the antibacterial article.

(4) A process for producing an antibacterial article according to any one of above items 2 and 3, wherein the alcohol is ethanol.

The present invention is described in the following.

Antibacterial articles of the present invention have high safety, provide the efficient and effective antibacterial effect of ε-polylysine used as a food preservative, and the articles are produced by adsorbing ε-polylysine on fibers, nonwoven fabrics, knitted or woven fabrics, films, sheets, plates, trays, vessels and the like.

DETAILED DESCRIPTION OF THE INVENTION

ε-polylysine used in the present invention is obtained by cultivating on media *Streptomyces albulus subsp, lysinopolymerus* belonging to a Streptomyces genus which is an ε-polylysine-producing micro-organism described in, for example, Japanese Laid-Open Patent Publication No. 59-20359, and separating and collecting ε-polylysine from the resulting culture medium.

In the present invention, ε-polylysine can be used as a free type or a salt type of an inorganic acid such as hydrochloric acid, sulfuric acid or phosphoric acid, or an organic acid such as acetic acid, propionic acid, fumaric acid, malic acid or citric acid. Both types of these salts of inorganic acids or organic acids as well as a free type have similar antibacterial effect.

As a method for adsorbing ε-polylysine on materials, there is an immersion treatment and spray treatment which can be effectively and easily used. In the immersion of nonwoven fabrics such as polyester-polypropylene nonwoven fabrics, the material is immersed in an aqueous solution of one % by weight of ε-polylysine or an aqueous solution of 60% by weight of ethanol containing 1% by weight of ε-polylysine for 30 seconds and air-dried. In the spray treatment, the material is sprayed with 0.5 g of an aqueous solution of 60% by weight of ethanol containing 0.5% by weight of ε-polylysine per 100 cm$^2$ of the material.

In the immersion treatment and the spray treatment, either of the aqueous solution including only ε-polylysine or the solution of ε-polylysine in alcohol such as ethanol or in an aqueous solution containing alcohol such as methanol or ethanol can be used. It is also possible to use a solution obtained by adding a surface-active agent and the like in the immersion treatment liquid or the spray treatment liquid. It is possible to add or simultaneously use other compounds having antibacterial activity such as a glyceryl fatty acid ester, organic or inorganic salts having multiple effects, pH adjustors, amino acids and the like.

The concentration of ε-polylysine in the aqueous solution or the alcohol solution or the aqueous solution containing an alcohol for the immersion treatment and the spray treatment is different depending upon the immersion time or the sprayed amount, typically 0.01–20% by weight is preferred.

Materials having water absorption properties are preferably used for the antibacterial articles of the present invention and, particularly, nonwoven fabrics, knitted or woven fabrics and paper fabricated from natural fibers such as cotton, silk and wool, and fibers, nonwoven fabrics, knitted or woven fabrics, films, sheets, plates, trays and containers fabricated from synthetic resins of thermoplastics such as polyvinyl chloride, polyvinylidene chloride, polyolefin resins, e.g., polyethylene and polypropylene, polyamide and polyester, without particular limit.

The antibacterial articles of the present invention are used for inhibiting proliferation of micro-organisms whenever the micro-organisms contact food and proliferate on the surface of food as a water absorbent sheet, wrapping materials, trays or the like. The antibacterial articles are also used for articles such as curtains, bed clothes, or several kinds of articles of clothing in which micro-organisms proliferate in organisms of dust, motes and sweat.

With regard to the curtains, bed clothes, or articles of clothing, knitted or woven fabrics and nonwoven fabrics are processed by immersion or spraying before or after sewing them. These articles are also contained in the antibacterial articles of the present invention.

DESCRIPTION OF THE PREFERRED EMBODIMENTS

The following tests and examples illustrate the present invention more specifically, but these will not always be precise in practical applications.

EXAMPLE 1

A nonwoven fabric made of polypropylene-polyethylene was cut into a size of 30 cm×30 cm and immersed in 100 ml of an aqueous solution of one % by weight of ε-polylysine for 30 seconds. Then, it was dried in a desiccator at 50° C. for one hour.

Comparative Example 1

The same nonwoven fabric made of the same material having the same size as in Example 1 was immersed in sterile water for 30 seconds and dried in a desiccator at 50° C. for one hour.

EXAMPLE 2

The same nonwoven fabric made of the same material having the same size as in Example 1 was uniformly sprayed with 1.5 g of an aqueous solution of 60% by weight of ethanol containing 0.5% by weight of ε-polylysine and then dried in a desiccator at 30° C. for 30 minutes.

Comparative Example 2

The same nonwoven fabric made of the same material having the same size as in Example 1 was uniformly sprayed with 1.5 g of aqueous solution of 60% by weight of ethanol and then dried in a desiccator at 30° C. for 30 minutes.

(Test 1)

Using the nonwoven fabric obtained in Example 1, Comparative example 1, Example 2 and Comparative example 2, antibacterial activity was tested.

Conventional agar medium was added to a plate having 90 mm diameter, and $10^4$ of *Escherichia coli* IFO 13500 was applied on the whole surface of the agar medium. Then, the nonwoven fabrics prepared in Examples 1 and 2 and Comparative Examples 1 and 2 were cut in a circle of 85 mm diameter. The sprayed surface of the nonwoven fabrics of Example 2 and Comparative example 2 were placed in contact on the medium, and the nonwoven fabrics of Example 1 and Comparative example 1 were placed in contact with the medium. In these conditions, these fabrics were maintained at 10° C. and 20° C. for 3 hours and 9 hours, respectively, and the fabrics were removed. Desoxycholate agar medium was added to cover on the conventional agar medium, and the number of living *E.coli* was determined. The results were shown in Table 1.

(Test 2) Using the nonwoven fabrics obtained in Example 1 and comparative example 1, antibacterial activity was tested. 0.2 g of cut nonwoven fabrics of Example 1 and Comparative example 1 were placed in a plate having 90 mm diameter. 0.2 ml of liquid of *Staphylococcus aureus* IFO 12732($5\times10^5$/ml) was applied to the nonwoven fabrics.

After culturing them at 37° C. for 18 hours, the number of bacteria were counted after culturing with a conventional agar medium at 37° C. for 24 hours. The number of bacteria were 10/g or less in Example 1 and $10^4$/g in Comparative example 1. The results show that the antibacterial article of the present invention has antibacterial activity by itself.

The merits of the present invention are as follows. Using the antibacterial articles obtained by immersing or spraying a small quantity of ε-polylysine on raw materials, it is possible to inhibit proliferation of micro-organisms on the food surface and keep the food fresh for a long term. Since the ε-polylysine scarcely contacts to the food surface, the taste of food is little affected. Since the articles are not directly added to food products, the physical properties of the food products are little changed. The articles can be preferably used for packing all sorts of the food products as a drip-adsorbing sheet, a wrapper for food, a food-packaging tray and a food container which are used as packaging materials for inhibiting proliferation of micro-organisms when the micro-organisms contact the food and proliferate on the food surface. The articles are also preferably used for inhibiting proliferation of the micro-organisms in organisms of dust, motes and sweat which adhere to curtains, bed clothes, or articles of clothing. The materials of the present invention, accordingly, have various safe uses.

TABLE 1

| Sample | Shelf temperature | Number of *E. coli* in a plate after 3 hours | 6 hours |
|---|---|---|---|
| Example 1 | 10° C. | $10^2$ | $10^1$ |
| Comparative example 1 | 10° C. | $10^4$ | $>10^4$ |
| Example 2 | 10° C. | $10^2$ | $10^1$ |
| Comparative example 2 | 10° C. | $10^3$ | $>10^4$ |
| Example 1 | 20° C. | $10^3$ | $10^1$ |
| Comparative example 1 | 20° C. | $10^4$ | $>10^4$ |
| Example 2 | 20° C. | $10^3$ | $10^1$ |
| Comparative example 2 | 20° C. | $10^3$ | $>10^4$ |

We claim:

1. An antibacterial article comprising a substrate selected from the group consisting of non-woven fabrics, knitted fabrics, and woven fabrics, wherein ε-polylysine is adsorbed on the substrate.

2. The antibacterial article of claim 1 wherein the substrate is a non-woven fabric made of polypropylene-polyethylene.

3. An antibacterial article comprising a substrate of paper fabricated from natural fibers selected from the group consisting of cotton, silk, and wool, wherein ε-polylysine is adsorbed on the substrate.

4. An antibacterial food wrapper including a substrate on which ε-polylysine is adsorbed.

5. An antibacterial article comprising a substrate of a synthetic resin selected from the group consisting of polyvinyl chloride, polyvinylidene chloride, polyolefin resins including polyethylene and polypropylene, polyamide, and polyester, wherein ε-polylysine is adsorbed on the substrate.

6. The antibacterial article of claim 5 wherein the article is a container for food.

7. A process for producing an antibacterial article comprising immersing a substrate of a non-woven polyester-polypropylene fabric in an aqueous solution of 1 weight percent of ε-polylysine.

8. A process for producing an antibacterial article comprising immersing a substrate of a non-woven polyester-polypropylene fabric in an aqueous solution of 60 weight percent of ethanol and 1 weight percent of ε-polylysine.

9. A process for producing an antibacterial article comprising spraying a substrate of a non-woven polyester-polypropylene fabric with an aqueous solution of 60 weight percent of ethanol and 0.5 weight percent of ε-polylysine in an amount of 0.5 grams per 100 $cm^2$ of area of the substrate.

* * * * *